United States Patent [19]

Hattori et al.

[11] 4,121,548

[45] Oct. 24, 1978

[54] DETERIORATED CONDITION DETECTING APPARATUS FOR AN OXYGEN SENSOR

[75] Inventors: Tadashi Hattori, Okazaki; Hiroaki Yamaguchi, Aichi; Takamichi Nakase, Gamagori, all of Japan

[73] Assignee: Nippon Soken, Inc., Nishio, Japan

[21] Appl. No.: 814,122

[22] Filed: Jul. 8, 1977

[30] Foreign Application Priority Data

Aug. 8, 1976 [JP] Japan .................................. 51-94119
Aug. 8, 1976 [JP] Japan .................................. 51-94123

[51] Int. Cl.² ........................................... F02B 3/00
[52] U.S. Cl. .................................. 123/32 EE; 73/23; 123/119 EC; 123/32 EH; 60/285; 60/276
[58] Field of Search ....... 123/119 EC, 32 EE, 32 EH, 123/124 B; 73/23; 60/285, 276

[56] References Cited

U.S. PATENT DOCUMENTS

| | | | |
|---|---|---|---|
| 3,926,154 | 12/1975 | Williams | 123/32 EE |
| 3,939,654 | 2/1976 | Creps | 123/119 EC |
| 3,984,976 | 10/1976 | Nagai | 60/285 |
| 4,019,470 | 4/1977 | Asano | 60/285 |
| 4,019,474 | 4/1977 | Nishianiya et al. | 123/32 EE |
| 4,027,477 | 6/1977 | Storey | 60/276 |
| 4,027,637 | 6/1977 | Aono | 123/32 EE |
| 4,029,061 | 6/1977 | Asano | 60/276 |
| 4,068,472 | 1/1978 | Takata et al. | 60/276 |

*Primary Examiner*—Charles J. Myhre
*Assistant Examiner*—R. A. Nelli
*Attorney, Agent, or Firm*—Cushman, Darby & Cushman

[57] ABSTRACT

A deteriorated condition detecting apparatus for an oxygen concentration sensor used in an air-fuel ratio feedback control for an internal combustion engine comprises a reference oxygen concentration sensor mounted in proximity to the oxygen concentration sensor used for the air-fuel ratio feedback control and a discriminator for comparing duty factors of output signals from those two sensors to determine a deteriorated condition of the oxygen sensor. The discriminator determines the deteriorated condition when the duty factor of the sensor under test deviates from the duty factor of the output signal of the reference sensor by a predetermined amount. It converts the outputs of the respective sensors to square wave signals and integrates one of the levels of the square wave signals to determine the duty factors, and differentially amplifies the integrated signal to produce a differential output signal, which is then compared with a predetermined level to determine whether there exists a deviation of the duty factor corresponding to the deteriorated condition.

5 Claims, 13 Drawing Figures

DETERIORATED CONDITION DETECTING APPARATUS FOR AN OXYGEN SENSOR

FIELD OF THE INVENTION

The present invention relates to a deteriorated condition detecting apparatus, and more particularly to a deteriorated condition detecting apparatus for an oxygen concentration sensor used in air-fuel ratio feedback control for an internal combustion engine.

DESCRIPTION OF THE PRIOR ART

Figure 1:
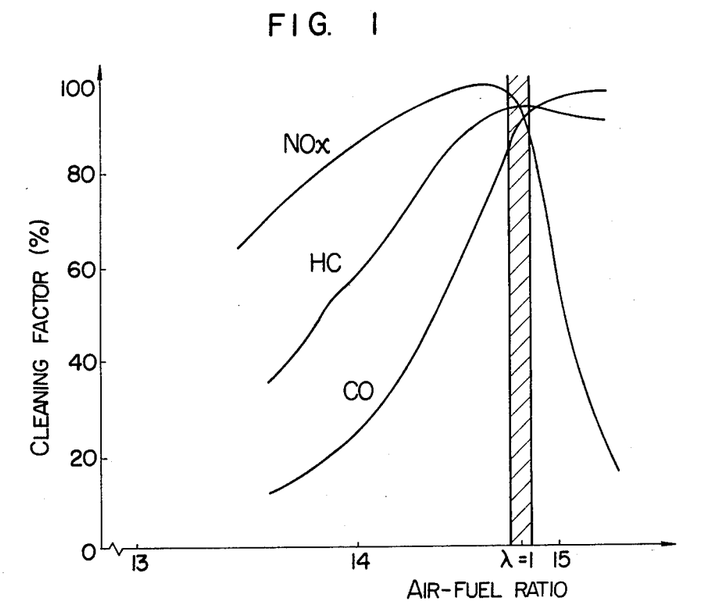
FIG. 1 shows characteristic curves of a cleaning factor relative to an air-fuel ratio for a ternary catalyst used to clean exhaust gas of an internal combustion engine.

It has been known to use a ternary catalyst to clean exhaust gas (particularly CO, HC and NOx) exhausted from an internal combustion engine of a motor vehicle. The ternary catalyst exhibits a high cleaning factor to noxious gas components CO, HC and Nox when an air-fuel ratio of air-fuel mixture is near a stoichiometric air-fuel ratio (air excess rate $\lambda = 1$) shown by hatching in FIG. 1. Accordingly, when the ternay catalyst is used to clean the exhaust gas of the internal combustion engine, it is necessary to precisely control the air-fuel ratio of the air-fuel mixture to be approximately equal to the stoichiometric air-fuel ratio in a suction system or an exhaust system of the internal combustion engine. In order to satisfy this requirement, it has been proposed to use feedback control of the air-fuel ratio.

Figure 2:
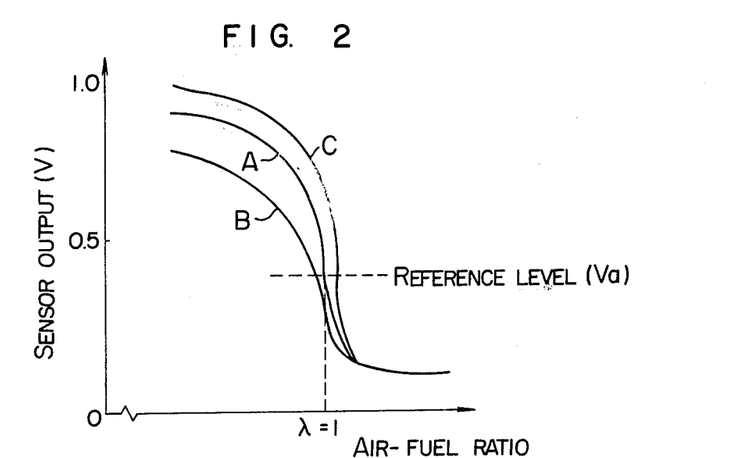
FIG. 2 shows characteristic curves of an output relative to the air-fuel ratio of an oxygen concentration sensor.

In the air-fuel ratio feedback control, an oxygen concentration sensor (hereinafter simply referred to as an $O_2$ sensor) made of an oxygen ion conductive metal oxide such as zirconium dioxide is used to sense the air-fuel ratio. As shown by a characteristic curve A in FIG. 2, this type of $O_2$ sensor produces a low level "O" signal when the air-fuel ratio of the air-fuel mixture is higher than the stoichiometric air-fuel ratio because oxygen exists in the exhaust gas, while it produces a high level "1" signal when the air-fuel ratio of the air-fuel mixture is lower than the stoichiometric air-fuel ratio because no oxygen exists in the exhaust gas. The output voltage level is changed substantially stepwise near the stoichiometric air-fuel ratio ($\lambda=1$). Since the $O_2$ sensor is mounted in the exhaust gas flow, an output characteristic thereof is deteriorated by the deposition of noxious component such as lead (Pb) in the exhaust gas. The deterioration of the output characteristic mainly results in (1) the increase of an internal resistance, (2) the decrease of an e.m.f., and (3) the increase of a response time. Once the $O_2$ sensor has been deteriorated, it is not possible to attain precise feedback control of the air-fuel ratio but the air-fuel ratio derived from the feedback control greatly deviates from a target air-fuel ratio, resulting in inefficiency of the internal combustion engine.

The deterioration of the output characteristic of the $O_2$ sensor is analized in detail below.

(1) Increase of internal resistance

Figure 3:
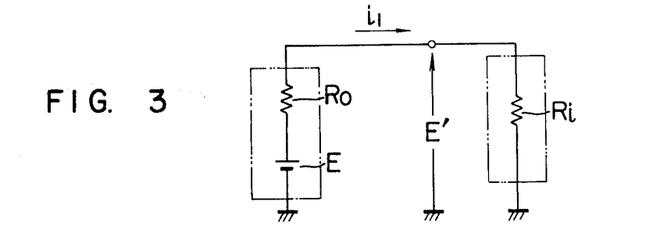
FIGS. 3 and 4 show equivalent circuits used to explain the operation of the oxygen concentration sensor.
Figure 4:
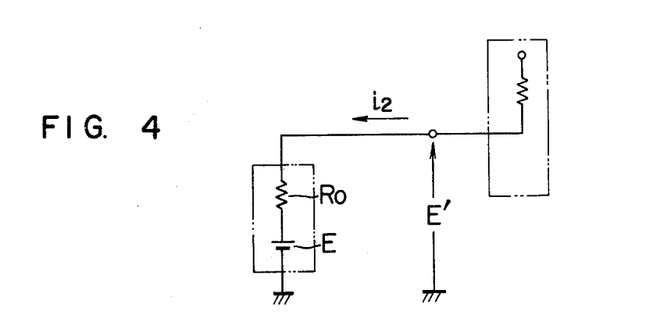

Referring to FIG. 3, when a current $i_1$ is supplied from the $O_2$ sensor to a control circuit, an apparent output voltage E' of the $O_2$ sensor is equivalently given by $E' = E \times R_i/(R_0 + R_i)$, where $R_0$ is the internal resistance of the $O_2$ sensor, E is the e.m.f. thereof, and $R_i$ is an input impedance of the control circuit which processes the output voltage of the $O_2$ sensor. Conversely, where a current $i_2$ is supplied from the control circuit to the $O_2$ sensor as shown in FIG. 4, an apparent output voltage of the $O_2$ sensor is equivalently given by $E' = E + R_0 \times i_2$. Accordingly, when the current $i_1$ flows out of the $O_2$ sensor, the output voltage E' of the $O_2$ sensor decreases as the internal resistance $R_0$ increases as shown by a characteristic curve B in FIG. 2 and the air-fuel ratio deviates to smaller side ($\lambda<1$; rich). Conversely, when the current $i_2$ flows into the $O_2$ sensor, the output voltage E' increases as the internal resistance $R_0$ increases as shown by a characteristic curve C in FIG. 2 and the air-fuel ratio deviates to larger side ($\lambda>1$, lean).

(2) Decrease of e.m.f.

In either of the systems shown in FIGS. 3 and 4, when the e.m.f. E of the $O_2$ sensor decreases, the output voltage E' of the $O_2$ sensor decreases as shown by the characteristic curve B in FIG. 2 and the air-fuel ratio deviates to the smaller side ($\lambda<1$, rich).

(3) Increase of response time

Figure 5:
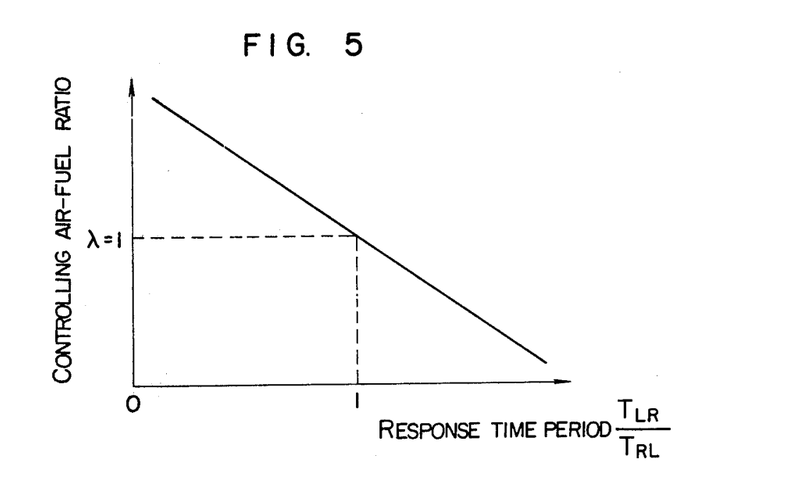
FIG. 5 shows a characteristic curve of the air-fuel ratio relative to a response time of the oxygen concentration sensor.

The increase of the response time of the $O_2$ sensor includes the increase of a response time $T_{LR}$ from the lean side (low level output voltage) to the rich side (high level output voltage) and the increase of a response time $T_{RL}$ from the rich side to the lean side. When the response time $T_{LR}$ increases, the air-fuel ratio deviates to the rich (R) side and when the response time $T_{RL}$ increases the air-fuel ratio deviates to the lean (L) side. As shown in FIG. 5, as a ratio ($T_{LR}/T_{RL}$) of the response time $T_{LR}$ to the response time $T_{RL}$ increases, the air-fuel ratio deviates to the rich side. If both the response time $T_{LR}$ and the response time $T_{RL}$ increase, the air-fuel ratio changes over a wide range and may deviate beyond the stoichiometric air-fuel ratio region shown by hatching in FIG. 1 which shows a high cleaning factor region.

Figure 6:
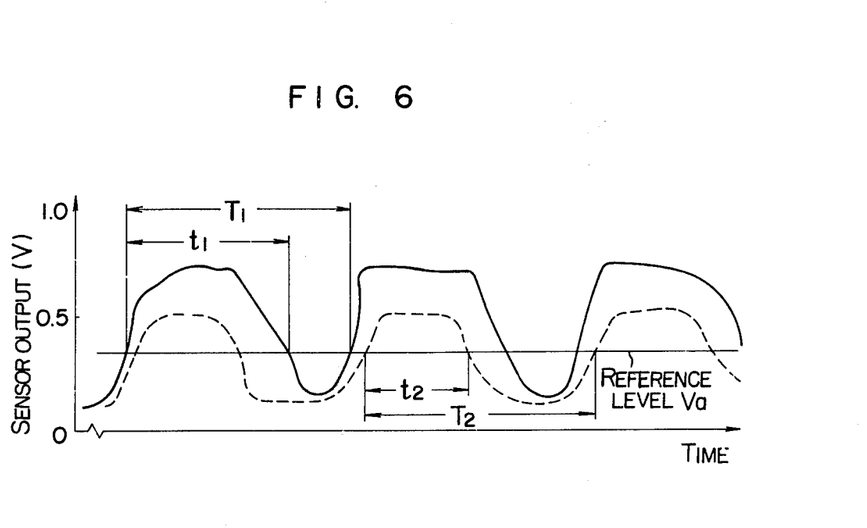
FIG. 6 shows signal waveforms illustrating change of output of the oxygen concentration sensor with time.

From the above three factors, the deterioration of the $O_2$ sensor can be determined. In this case, an output voltage waveform of the $O_2$ sensor may be used to determine the deterioration. More particularly, the output waveform of a normal $O_2$ sensor is shown by a broken line in FIG. 6 and it exhibits a duty factor $d_2$ which is defined by $t_2/T_2$. On the otherhand, an output waveform of an $O_2$ sensor which has been deteriorated to deviate the air-fuel ratio to the lean side is shown by a solid line in FIG. 6 and it exhibits a duty factor $d_1$ which is defined by $t_1/T_1$. If $T_1=T_2$, then the duty factor $d_1$ is larger than the duty factor $d_2$. Conversely, the duty factor $d_1$ of an $O_2$ sensor which tends to deviates the air-fuel ratio to the rich side is smaller than the duty factor $d_2$ provided that $T_1=T_2$. Thus, since the relation between the output voltage of the $O_2$ sensor and the duty factor is such that the duty factor increases as the output voltage increases, the deteriorated condition of the $O_2$ sensor can be determined by measuring the duty factor $d$ of the output waveform of the $O_2$ sensor. If the general response of the $O_2$ sensor is deteriorated, the period T of the output waveform is elongated. Accordingly, the deteriorated condition of the $O_2$ sensor may be determined by measuring the period T.

SUMMARY OF THE INVENTION

It is an object of the present invention to provide a deteriorated condition detecting apparatus wherein an $O_2$ sensor which is to be tested for deteriorated condition and a reference sensor are mounted at the same place, one of the sensors is maintained under a feedback control operation condition for the air-fuel ratio, and duty factors of the output signals of the $O_2$ sensor under test and the reference $O_2$ sensor are compared to determine the deteriorated condition of the $O_2$ sensor under test.

it is another object of the present invention to provide a deteriorated condition detecting apparatus wherein mean values of duty factors of the output signals of the $O_2$ sensor under test and the reference $O_2$ sensor are compared to determine the deteriorated condition of the $O_2$ sensor under test.

DESCRIPTION OF THE PREFERRED EMBODIMENTS

Figure 7:
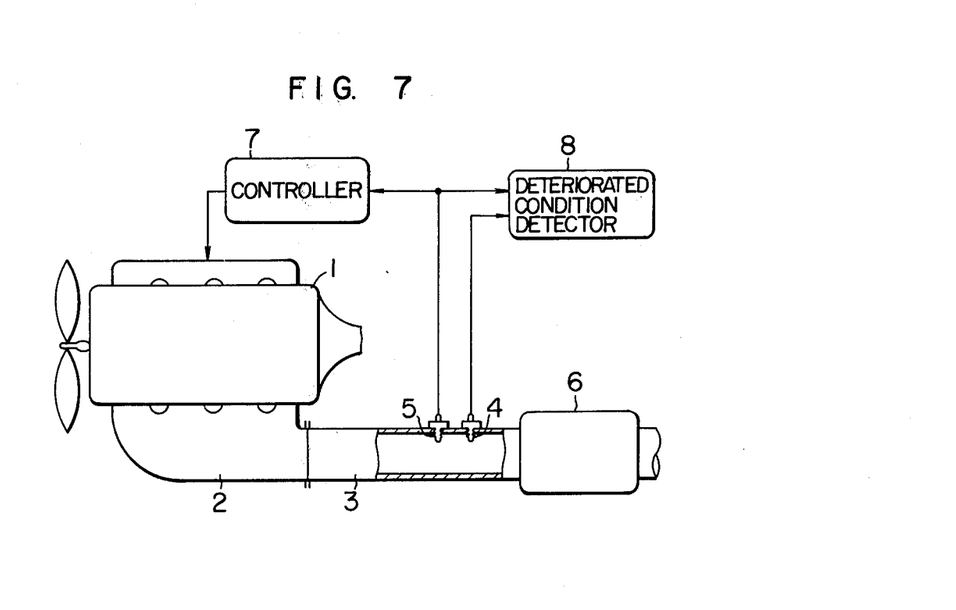
FIG. 7 is a schematic diagram illustrating an overall construction of a deteriorated condition detecting apparatus of the present invention.

The present invention is now explained in conjunction with the preferred embodiments thereof shown in FIGS. 7 through 13. Referring to FIG. 7 which shows an overall construction of the present invention, an application of the $O_2$ sensor to the air-fuel ratio control of an internal combustion engine is shown, in which numeral 1 denotes the internal combustion engine, 2 denotes an exhaust manifold of the internal combustion engine 1, 3 denotes an exhaust pipe, 4 denotes a reference $O_2$ sensor, 5 denotes an $O_2$ sensor to be tested, 6 denotes a ternary catalyst, 7 denotes a controller for processing an output signal of the $O_2$ sensor 5 under test to control an air-fuel ratio of air-fuel mixture in a suction system or an exhaust system, and 8 denotes a deteriorated condition detector for detecting deteriorated condition of the $O_2$ sensor 5 under test by comparing the output signals of the reference $O_2$ sensor 4 and the $O_2$ sensor 5 under test. In the above construction, the reference $O_2$ sensor 4 and the $O_2$ sensor 5 under test are arranged at substantially the same position on the exhaust pipe 3. A construction of the feedback control system using the $O_2$ sensor 5 has been known in the art and it is not explained here.

Figure 8:
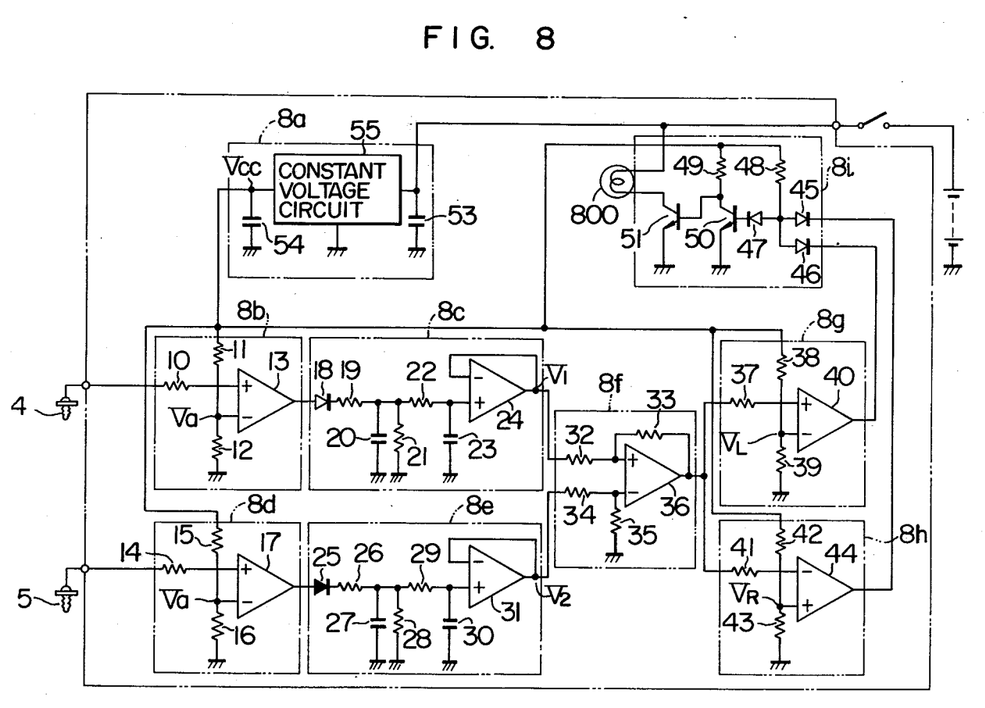
FIG. 8 shows an electrical circuit diagram illustrating one embodiment of the present apparatus shown in FIG. 7.

Detail of the deteriorated condition detector 8 is shown in FIG. 8, in which numeral 8a denotes a constant voltage circuit, 8b and 8d denote air-fuel ratio discrimination circuit for shaping output voltages of the reference $O_2$ sensor 4 and the $O_2$ sensor 5 under test, 8c and 8e denote integration circuits for measuring duty factors by the shaped voltages, 8f denotes a differential amplifier circuit for measuring a difference between the duty factors by the voltages derived from the integration circuits 8c and 8e, 8g and 8h denote air-fuel ratio deviation detecting circuits for detecting deviation of the air-fuel ratio by the voltage derived from the differential amplifier circuit 8f, and 8i denotes a logical determination circuit for determining the deterioration of the $O_2$ sensor 5 under test by the voltages derived from the air-fuel ratio deviation detecting circuits 8g and 8h. A lamp 800 for warning of the deterioration is connected to the logical determination circuit 8i.

The constant voltage circuit 8a comprises capacitors 53 and 54 and a voltage regulator 55 and it supplies a constant voltage $V_{cc}$.

The air-fuel ratio discrimination circuit 8b comprises resistors 10, 11 and 12 and a comparator 13, and it establishes a reference air-fuel ratio voltage $V_a$ corresponding to the stoichiometric air-fuel ratio by the voltage division by the resistors 11 and 12. This reference voltage is applied to an inverting input (−) terminal of the comparator 13 while an output voltage of the reference $O_2$ sensor 4 is applied to a non-inverting input (+) terminal of the comparator 13 through the resistor 10. Accordingly, the air-fuel ratio discrimination circuit 8b produces a "1" voltage when the air-fuel ratio is low (rich), that is, when oxygen is not present in the exhaust gas; and produces a "O" voltage when the air-fuel ratio is high (lean), that is, when oxygen is present in the exhaust gas.

Figure 9:
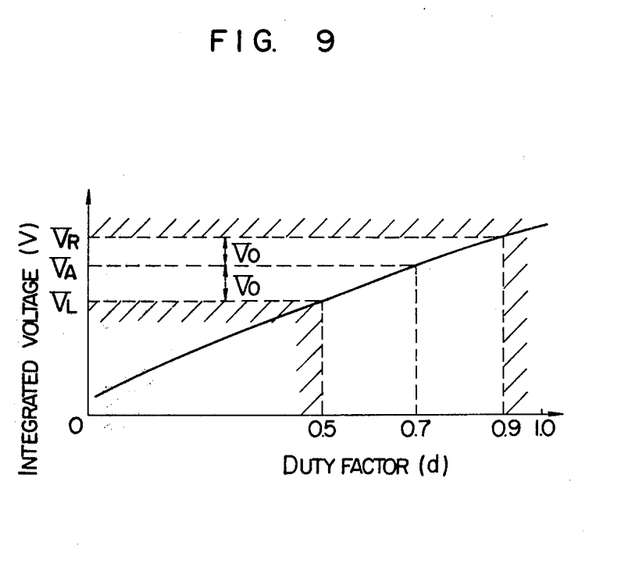
FIG. 9 shows a characteristic chart illustrating an integrated output relative to a duty factor, used to explain the operation of the embodiment shown in FIG. 8.

The integration circuit 8c comprises a diode 18, resistors 19, 21 and 22, capacitors 20 and 23 and an operational amplifier 24 and it integrates the "1" voltage of the air-fuel ratio discrimination circuit 8b. An integrated voltage $V_1$ at the output of the operational amplifier 24 which functions as the voltage follower circuit is substantially proportional to the duty factor $d$ of the output voltage of the reference $O_2$ sensor 4, as shown in FIG. 9.

The air-fuel ratio discrimination circuit 8d comprises resistors 14, 15 and 16 and a comparator 17. Like in the air-fuel ratio discrimination circuit 8b, the output voltage of the $O_2$ sensor 5 under test is applied to a non-inverting input terminal of the comparator 17 through the resistor 14 while the reference voltage $V_a$ is applied to an inverting input terminal so that either "1" or "O" voltage is produced depending on the output voltage of the $O_2$ sensor 5 under test.

The integration circuit 8e comprises a diode 25, resistors 26, 28 and 29, capacitors 27 and 30 and an operational amplifier 31, and it integrates the "1" voltage of the air-fuel ratio discrimination circuit 8d. Accordingly, an integrated voltage $V_2$ is substantially proportional to the duty factor $d$ of the output voltage of the $O_2$ sensor 5, as shown in FIG. 9.

The differential amplifier circuit 8f comprises resistors 32, 33, 34 and 35 and an operational amplifier 36, in which the resistances of the resistors 32 and 34 are equal to each other while the resistances of the resistors 33 and 35 are equal to each other. Accordingly, gain K of the differential amplifier circuit 8f is given by K = (resistance of the resistor 33)/(resistance of the resistor 32), and the two integrated voltages $V_1$ and $V_2$ are differentially amplified with the gain K resulting in an output voltage equal to $(V_{cc}/2) + K(V_1 - V_2)$.

The air-fuel ratio deviation detecting circuit 8g comprises resistors 37, 38 and 39 and a comparator 40, and it establishes a reference voltage $V_L$ by the resistors 38 and 39, which reference voltage $V_L$ is used to determine that a controlling air-fuel ratio resulting from the feedback control of the air-fuel ratio by the $O_2$ sensor 5 under test exhibits a tendency of leanness. On the other hand, the air-fuel ratio deviation detecting circuit 8h comprises resistors 41, 42 and 43 and a comparator 44, and it establishes a reference voltage $V_R$ by the resistors 42 and 43, which reference voltage is used to determine that the controlling air-fuel ratio by the $O_2$ sensor 5 under test exhibits a tendency of richness.

Let it assume that the duty factor d of the output voltage of the reference $O_2$ sensor 4 is 0.7, and that if the duty factor d of the output voltage of the $O_2$ sensor 5 exceeds 0.9, it is determined that the $O_2$ sensor 5 is in the deteriorated condition which results in high (lean) air-fuel ratio and if the duty factor d of the output voltage of the $O_2$ sensor 5 falls below 0.5, it is determined that the $O_2$ sensor 5 is in the deteriorated condition which results in low (rich) air-fuel ratio. Further assume that the integrated voltage $V_1$ is equal to $V_A$ when the duty factor d of the output voltage of the reference $O_2$ sensor 4 is equal to 0.7. Then, as shown in FIG. 9, when the integrated voltage $V_2$ associated with the $O_2$ sensor 5 is larger than $V_A + V_O$, the $O_2$ sensor 5 is in the deteriorated condition which results in a too lean air-fuel ratio, and when the integrated voltage $V_2$ is smaller than $V_A - V_O$, the $O_2$ sensor 5 is in the deteriorated condition which results in a too rich air-fuel ratio. The voltage $V_O$ is a constant voltage. Thus, the reference voltage $V_L$ determined by the dividing resistors 38 and 39 of the air-fuel ratio deviation detecting circuit 8g is established at $(V_{cc}/2) - K \cdot V_O$ and the reference voltage $V_R$ determined by the dividing resistors 42 and 43 of the air-fuel ratio deviation detecting circuit 8h is established at $(V_{cc}/2) + K \cdot V_o$.

Accordingly, the air-fuel ratio deviation detection circuits 8g and 8h can determine the deteriorated condition by the duty factor d of the output voltage of the $O_2$ sensor 5. If the duty factor d of the $O_2$ sensor 5 satisfies $0.5 < d < 0.9$, both of the air-fuel ratio deviation detecting circuits 8g and 8h produce "1" voltages indicating that the $O_2$ sensor 5 is not in the deteriorated condition. However, if the duty factor d of the $O_2$ sensor 5 satisfies $d > 0.9$, the air-fuel ratio deviation detecting circuit 8g produces the "0" voltage, and if the duty factor d of the $O_2$ sensor 5 satisfies $d < 0.5$, the air-fuel ratio deviation detecting circuit 8h produces the "0" voltage, indicating that the $O_2$ sensor 5 is in the deteriorated condition.

The logical determination circuit 8i comprises diodes 45, 46 and 47, resistors 48 and 49 and transistors 50 and 51. When at least one of the air-fuel ratio deviation detecting circuits 8g and 8h produces the "0" voltage, the transistors 50 and 51 are rendered non-conductive and conductive, respectively, and the lamp 800 is lit to warn of the deteriorated condition of the $O_2$ sensor 5 under test.

Figure 10:
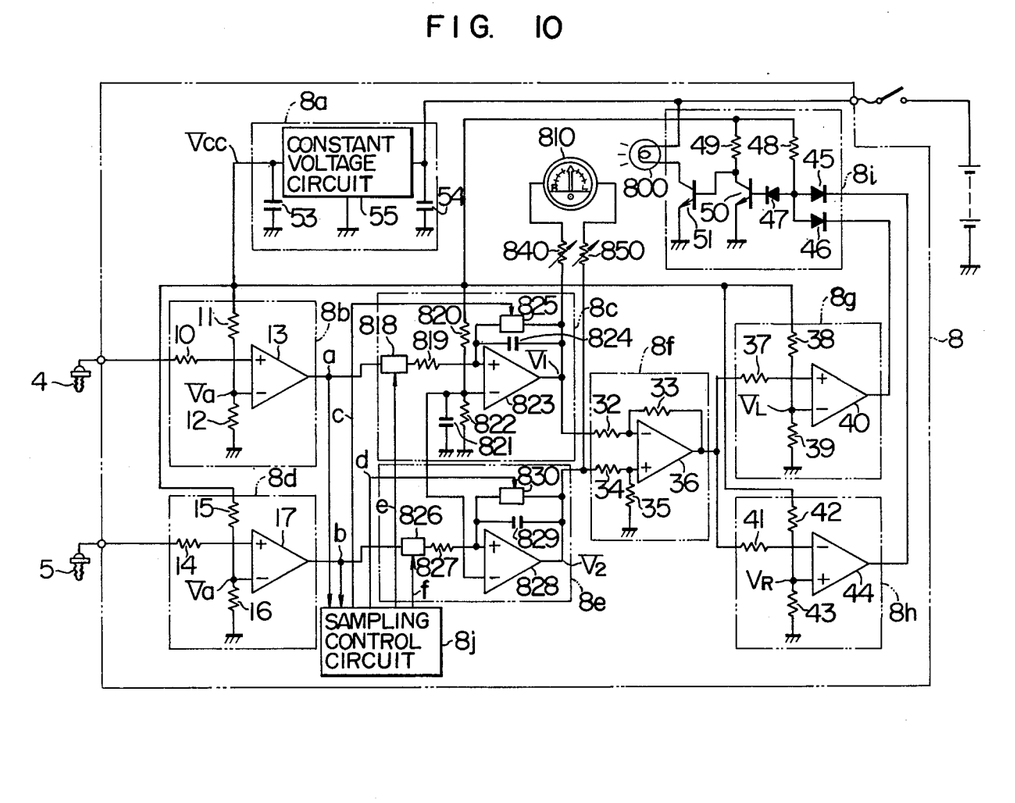
FIG. 10 shows an electrical circuit diagram illustrating a second embodiment of the present apparatus shown in FIG. 7.
Figure 11:
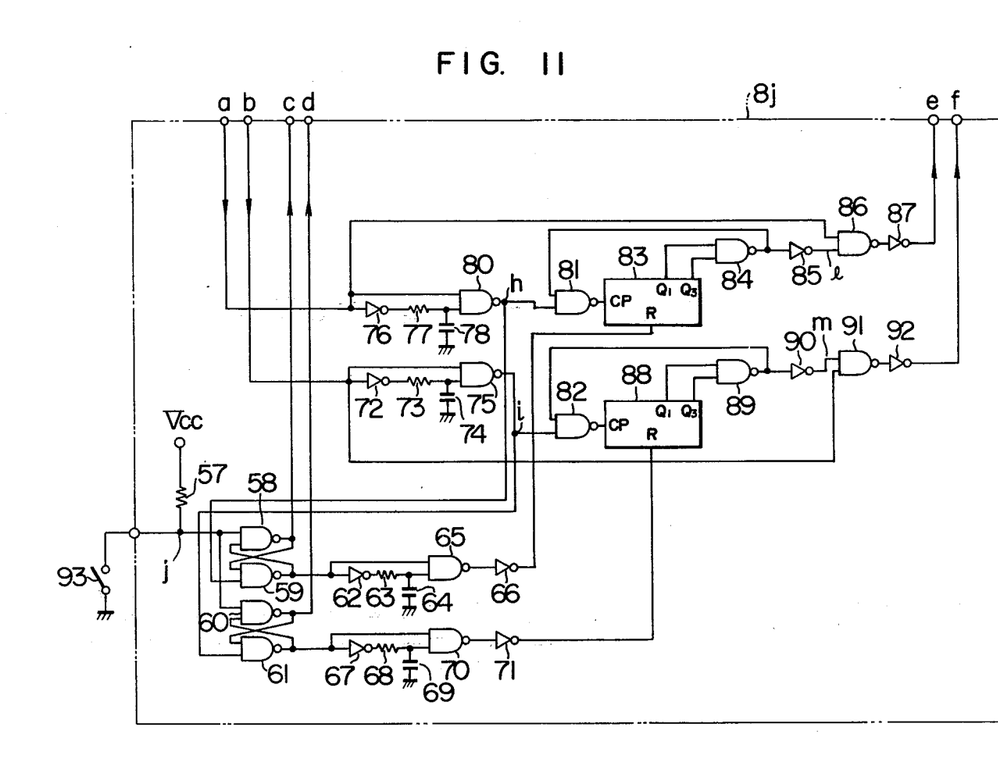
FIG. 11 shows an electrical circuit diagram illustrating detail of a sampling control circuit shown in FIG. 10.
Figure 12:
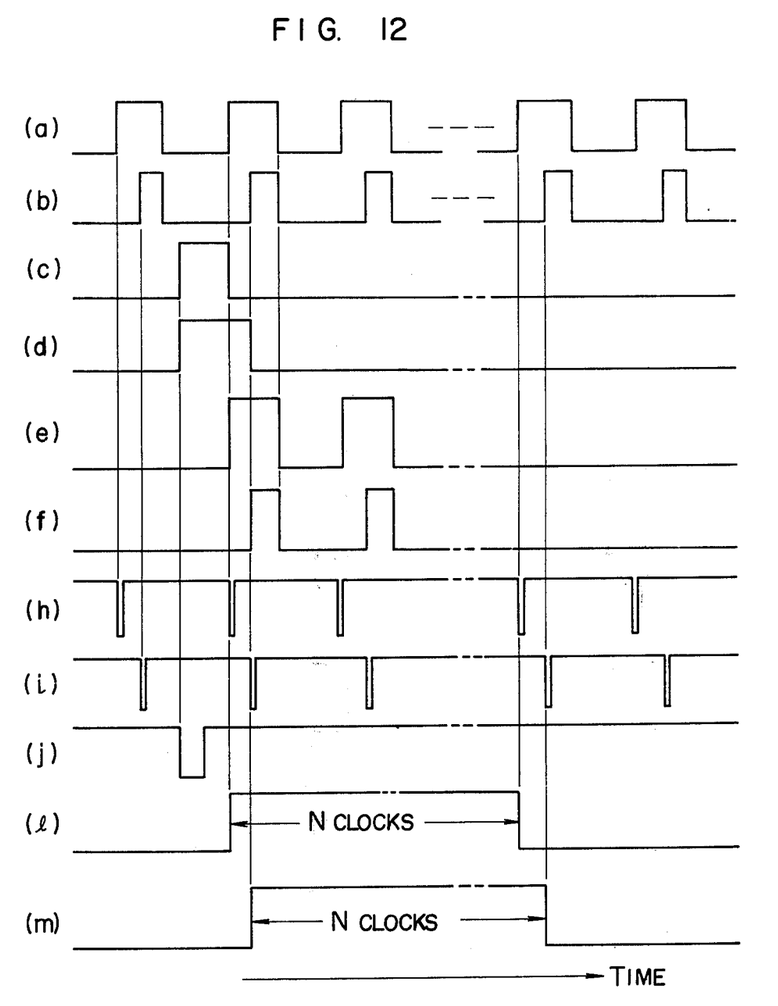
FIG. 12 shows signal waveforms used to explain the operation of the sampling control circuit shown in FIG. 11.

Referring now to FIGS. 10 through 12, a second embodiment of the present invention is explained. The same reference numerals are used therein to denote the same parts as those in the first embodiment shown in FIG. 8. The difference between the second embodiment shown in FIG. 10 and the first embodiment shown in FIG. 8 lies in that the construction of the integration circuits 8c and 8e, a sampling circuit 8j for controlling the integration circuits 8c and 8e and a meter 810 for analog indication of the deteriorated condition are additionally provided. The description with regard to constructions and operation of the constant voltage circuit 8a, the air-fuel ratio discrimination circuits 8b and 8d, the differential amplifier circuit 8f, the air-fuel ratio deviation detecting circuits 8g and 8h and the logical determination circuit 8i are omitted here.

Referring to FIG. 11, the sampling control circuit 8j is explained. A terminal a is connected to a monostable multivibrator circuit comprising an inverter 76, a resistor 77, a capacitor 78 and a NAND gate 80. The monostable multivibrator produces a signal shown in FIG. 12 (h) at a point h when the output voltage of the air-fuel ratio discrimination circuit 8b (shown in FIG. 12(a)) is switched to the "1" voltage.

The monostable multivibrator is connected to a counter circuit comprising NAND gates 81, 84 and 86, a counter 83 and inverters 85 and 87. The signal produced at the point h is applied through the NAND gate 81 as a clock pulse, which is counted by the counter 83. The counter 83 continues to count the clock pulse until the count thereof reaches a predetermined N count, and further counting is inhibited by the NAND gates 81 and 84. Accordingly, a "1" voltage appears at a point l as shown in FIG. 12(l) during the counting mode of the counter 83, and N signals which are identical to those shown in FIG. 12(a) appear at a terminal e as shown in FIG. 12(e).

A terminal b is connected to a monostable multivibrator circuit comprising an inverter 72, a resistor 73, a capacitor 74 and a NAND gate 75. This monostable multivibrator produces a signal shown in FIG. 12(i) at a point i when the output voltage of the air-fuel ratio discrimination circuit 8d (shown in FIG. 12(b)) is switched to the "1" voltage.

This monostable multivibrator circuit is connected to a counter circuit comprising NAND gates 82, 89 and 91, a counter 88 and inverters 90 and 92. The signal produced at the point i is applied through the NAND gate 82 as a clock pulse, which is counted by the counter 88. Like the counter 83, the counting operation of the counter 88 is limited to the N count and the signals shown in FIGS. 12(m) and 12(f) appear at terminals m and f, respectively. The signal appearing at the terminal f is identical to that applied to the terminal b and has N signals.

In FIG. 11, numeral 93 denotes a switch, which is connected to a flip-flop comprising NAND gates 58 and 59, and to a flip-flop comprising NAND gates 60 and 61. The switch 93 commands the initiation of the count operation of the counters 83 and 88. When the switch 93 is closed, the point j to which the constant voltage $V_{cc}$ has been applied through a resistor 57, assumes "0" voltage as shown in FIG. 12(j). The flip-flop comprising the NAND gates 58 and 59 and the flip-flop comprising the NAND gates 60 and 61 are set by this signal, and the counter 83 is reset by a monostable multivibrator circuit comprising inverters 63 and 66, a resistor 63, a capacitor 64 and a NAND gate 65 while the counter 88 is reset by a monostable multivibrator circuit comprising inverters 67 and 71, a resistor 68, a capacitor 69 and a NAND gate 70. Since the above two flip-flops are reset by the signals at the points h and i, signals shown in FIGS. 12(c) and 12(d) appear at terminals c and d, respectively.

The integration circuits 8c and 8e which are controlled by the sampling control circuit 8j shown in FIG. 11 are illustrated in FIG. 10. The integration circuit 8c comprises analog switches 818 and 825, resistors 819, 820 and 822, a capacitor 821 and an operational amplifier 823. While the terminal c of the sampling control circuit 8j assumes the "1" voltage, the analog switch 825 is closed to discharge the capacitor 824. Thereafter, while the terminal e assumes the "1" voltage, the analog switch 818 is closed to apply the output voltage from the air-fuel ratio discrimination circuit 8b. Namely, the "1" voltage produced by the air-fuel ratio discrimination circuit 8b is sampled N times and the sampled signals are integrated. Accordingly, the integrated voltage $V_1$ produced by the integration circuit 8c is proportional to the duration of the "1" voltage applied via the analog switch 818, and is proportional to a mean value of the duty factor of the output signal of the reference $O_2$ sensor 4.

The integration circuit 8e comprisis analog switches 826 and 830, a resistor 827, an operational amplifier 828 and a capacitor 829. Like the integration circuit 8c, the integration of the integration circuit 8e is controlled by the sampling control circuit 8j and the integrated voltage $V_2$ is proportional to a mean value of the duty factor of the output signal of the $O_2$ sensor 5 under test. The meter 810 gives an indication corresponding to a differential voltage between the two integrated voltages $V_1$ and $V_2$ applied through the resistors 840 and 850 to analog indicate a degree of the deterioration of the $O_2$ sensor 5 relative to the reference $O_2$ sensor 4.

Figure 13:
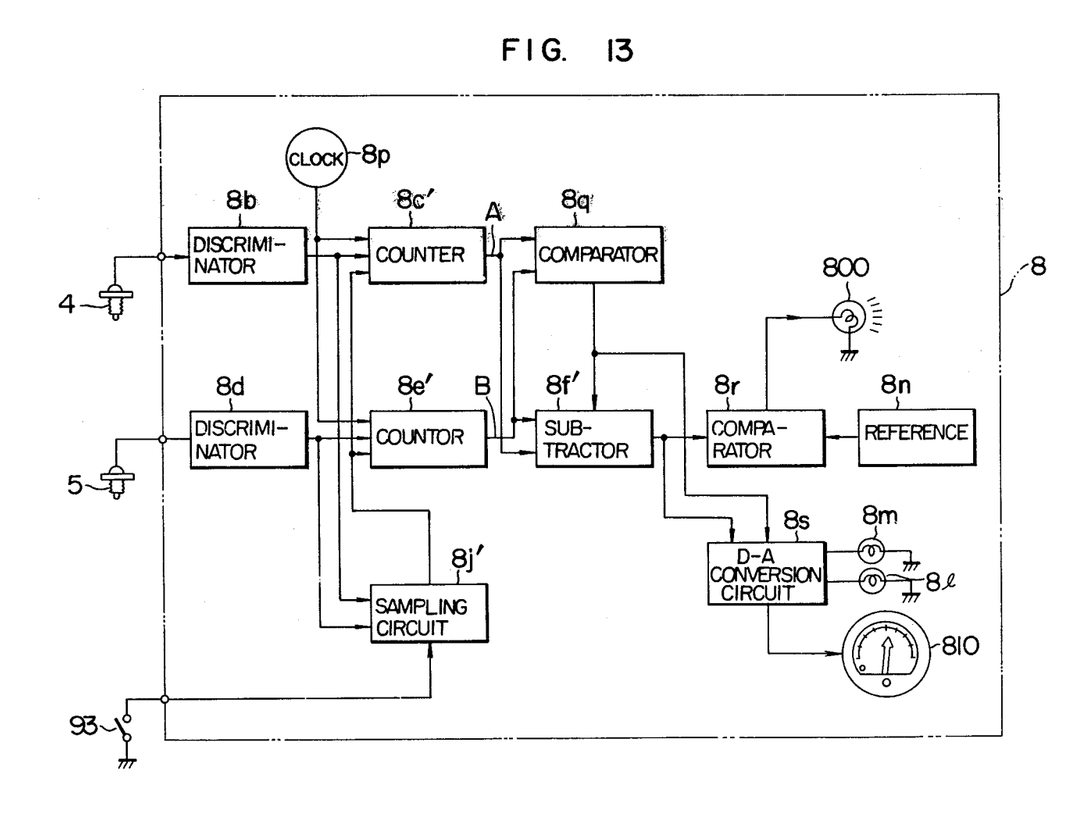
FIG. 13 is a block diagram illustrating a third embodiment of the present apparatus shown in FIG. 7.

While the first and second embodiments explained above detect the deterioration of the $O_2$ sensor 5 under test by analog operation, digital operation may be used. An example therefor is shown in FIG. 13, in which counter circuits 8c' and 8e' (RCA CD4040) count clock pulses from a clock generator 8p while the output voltages of the air-fuel ratio discrimination circuits 8b and 8d maintain a given level, and a sampling control circuit 8j' controls N times of repetition of the above operation. A comparator 8q (RCA CD 4063) compares the counts A and B of the counter circuits 8c' and 8e' and issues a subtraction command (A–B) or (B–A) to a subtraction circuit (RCA CD4008) depending on the comparison result. Accordingly, the subtraction circuit 8f' produces a difference of (A–B) representative of a derivation between the duty factors of the two $O_2$ sensors 4 and 5. The difference is compared with a reference value from a reference deviation setting circuit 8n by a compare circuit 8r, and when the deviation exceeds the reference value the lamp 800 is lit to warn the deterioration of the $O_2$ sensor 5 under test. The difference is further converted to an analog voltage by a D-A conversion circuit 8s and a degree of the deterioration is analog indicated by the meter 810'. Lamp 8l or 8m is lit depending on the output of the comparator circuit 8q and the difference to indicate whether the $O_2$ sensor 5 under test is in the deteriorated condition which results in a rich air-fuel ratio or in the deteriorated condition which results in a lean air-fuel ratio.

While three embodiments of the present invention have been explained, the value of the duty factor d for determining the deteriorated condition and the range of determination may be set freely as required. The sampling of the duty factor may be effected while the $O_2$ sensor is detecting a lean air-fuel ratio, and the deteriorated condition of the $O_2$ sensor under test may be determined while the reference $O_2$ sensor 4 is held under the air-fuel ratio feedback condition.

The $O_2$ sensors 4 and 5 need not necessarily be mounted in the exhaust pipe 3 but the feedback control of the air-fuel ratio may be effected using model gas to detect the deteriorated condition.

Furthermore, although the above embodiments use $O_2$ sensors made of oxygen ion conductive metal oxide such as zirconium dioxide, a sensor made of a transition metal oxide such as titanium dioxide, an electrical resistance of which changes with gas components in the exhaust gas, may be used to detect the deteriorated condition in a similar manner.

What is claimed is:

1. A deteriorated condition detecting apparatus for oxygen sensors comprising:

an oxygen sensor, positioned to be tested in a gaseous atmosphere in which oxygen concentration changes, for detecting the presence and the absence of oxygen in said gaseous atmosphere;

a reference sensor, positioned near said oxygen sensor and adapted to be correctly responsive to the oxygen concentration in said gaseous atmosphere, for detecting the presence and the absence of oxygen in said gaseous atmosphere;

first comparing means, connected to said oxygen sensor, for generating a first comparison signal which changes the signal level thereof between two constant levels, one and the other thereof being indicative of the presence and the absence of oxygen respectively;

second comparing means, connected to said reference oxygen sensor, for generating a second comparison signal which changes the signal level thereof in the same manner as said first comparison signal;

first integrating means, connected to said first comparing means, for generating a first integration signal which increases as the duty factor of said first comparison signal increases;

second integrating means, connected to said second comparing means, for generating a second integration signal which increases as the duty factor of said second comparison signal increases;

differential means, connected to said first and second integrating means, for generating a differential signal proportional to the difference between said first and second integration signals;

third comparing means, connected to said differential means, for generating a third comparison signal when said differential signal deviates from a predetermined reference level by more than a predetermined value; and warning means, connected to said third comparing means, for warning the deteriorated condition of said oxygen sensor in response to said third comparison signal.

2. A deteriorated condition detecting apparatus according to claim 1, wherein said oxygen sensor and said reference oxygen sensor are positioned in the exhaust passage of an engine, and wherein either one of said oxygen sensors is adapted to control the air-fuel mixture of said engine toward the stoichiometric ratio in response to the presence and the absence of oxygen in said exhaust passage.

3. A deteriorated condition detecting apparatus according to claim 2, wherein said third comparing means includes:

a first comparator for comparing said differential signal with a first reference level preset to be higher than said predetermined reference level by said predetermined value; and a second comparator for comparing said differential signal with a second reference level preset to be lower than said predetermined reference level by said predetermined value.

4. A deteriorated condition detecting apparatus according to claim 3 further comprising:

first sampling control means, connected between said first comparing means and said first integrating means, for controlling the numbers of said first comparison signal applied to said first integrating means to a predetermined number, whereby said first integration signal is controlled to be indicative of the average duty ratio of said first comparison signal; and second sampling control means, connected between said second comparing means and said second integrating means, for controlling the numbers of said second comparison signal applied to said second integrating means to said predetermined number, whereby said second integration signal is controlled to be indicative of the average duty ratio of said second comparison signal.

5. A deteriorated condition detecting apparatus according to claim 4 further comprising:

an indicating meter, connected to said first and second integrating means, for indicating in analog the deteriorated condition of said oxygen sensor in response to said first and second integrating means.

* * * * *